(12) United States Patent
Stad et al.

(10) Patent No.: US 8,679,126 B2
(45) Date of Patent: *Mar. 25, 2014

(54) TORQUE LIMITED INSTRUMENT FOR MANIPULATING A SPINAL ROD RELATIVE TO A BONE ANCHOR

(75) Inventors: Shawn D Stad, Fall River, MA (US); Raymond Murphy, Attlebro, MA (US)

(73) Assignee: DePuy Synthes Products, LLC, Raynham, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/444,430

(22) Filed: Apr. 11, 2012

(65) Prior Publication Data

US 2012/0221058 A1 Aug. 30, 2012

Related U.S. Application Data (63) Continuation of application No. 12/465,098, filed on May 13, 2009, now Pat. No. 8,206,394.

(51) Int. Cl.
*A61B 17/70* (2006.01)

(52) U.S. Cl.
USPC .................................................. 606/86 A

(58) Field of Classification Search
USPC ........................................ 606/86 A, 86 R, 99
See application file for complete search history.

(56) References Cited

U.S. PATENT DOCUMENTS

| | | |
|---|---|---|
| 410,780 A | 9/1889 | Cahn |
| 1,470,313 A | 10/1923 | Woolen |
| 1,628,144 A | 5/1927 | Herrmann |
| 1,709,766 A | 4/1929 | Bolton |
| 1,889,330 A | 11/1932 | Humes |
| 1,925,385 A | 9/1933 | Humes |
| 2,248,054 A | 7/1941 | Becker |
| 2,248,057 A | 7/1941 | Bond |
| 2,291,413 A | 7/1942 | Siebrandt |
| 2,370,407 A | 2/1945 | McCartney |
| 2,800,820 A | 7/1957 | Retterath |
| 3,677,378 A | 7/1972 | Troeger |
| 3,960,147 A | 6/1976 | Murray |

(Continued)

FOREIGN PATENT DOCUMENTS

| | | |
|---|---|---|
| DE | 4238339 | 5/1994 |
| DE | 2980656 | 7/1998 |

(Continued)

OTHER PUBLICATIONS

US Patent No. 6790209 Reissue Application Declaration and related Transmittal Letter and Information Disclosure Statement citing schematic drawings from Sofamor, "Introducteur-Contreur De Tige", Jan. 1, 1994.

*Primary Examiner* — Ellen C Hammond
*Assistant Examiner* — Atiya Mahmud (57) ABSTRACT

An instrument for adjusting a spinal rod relative to a bone anchor includes a handle connecting a set screw driver with a reduction collar. The handle includes an inner shaft engageable with the set screw driver, an outer shaft engageable with the reduction collar, and a clutch connecting the inner shaft to the outer shaft and permitting selective rotation of the inner shaft relative to the outer shaft, and thus, selective rotation of the set screw driver relative to the reduction collar, upon application of a torque to the reduction collar and the outer shaft greater than a preselected torque value.

21 Claims, 5 Drawing Sheets

(56) References Cited

U.S. PATENT DOCUMENTS

| | | |
|---|---|---|
| 4,237,875 A | 12/1980 | Termanini |
| 4,271,836 A | 6/1981 | Bacal |
| 4,411,259 A | 10/1983 | Drummond |
| 4,445,513 A | 5/1984 | Ulrich |
| 4,655,223 A | 4/1987 | Kim |
| 4,809,695 A | 3/1989 | Gwathmey |
| 4,896,661 A | 1/1990 | Bogert |
| 5,014,407 A | 5/1991 | Boughten |
| 5,020,519 A | 6/1991 | Hayes |
| 5,304,179 A | 4/1994 | Wagner |
| 5,306,248 A | 4/1994 | Barrington |
| 5,306,275 A | 4/1994 | Bryan |
| 5,364,397 A | 11/1994 | Hayes |
| 5,391,170 A | 2/1995 | McGuire |
| 5,429,641 A | 7/1995 | Gotfried |
| 5,484,437 A | 1/1996 | Michelson |
| 5,484,440 A | 1/1996 | Allard |
| 5,489,307 A | 2/1996 | Kuslich |
| 5,505,732 A | 4/1996 | Michelson |
| 5,545,165 A | 8/1996 | Biedermann |
| 5,551,320 A | 9/1996 | Horobec |
| 5,616,143 A | 4/1997 | Schlapfer |
| 5,649,931 A | 7/1997 | Bryant |
| 5,651,579 A | 7/1997 | Krieger |
| 5,697,933 A | 12/1997 | Gundlapalli |
| 5,707,371 A | 1/1998 | Metz-Stavenhagen |
| 5,720,751 A | 2/1998 | Jackson |
| 5,725,532 A | 3/1998 | Shoemaker |
| 5,746,757 A | 5/1998 | McGuire |
| 5,782,831 A | 7/1998 | Sherman |
| 5,810,878 A | 9/1998 | Burel |
| 5,814,046 A | 9/1998 | Hopf |
| 5,910,141 A | 6/1999 | Morrison |
| 5,941,885 A | 8/1999 | Jackson |
| 5,951,564 A | 9/1999 | Schroder |
| 6,010,509 A | 1/2000 | Delgado |
| 6,036,692 A | 3/2000 | Burel |
| 6,099,528 A | 8/2000 | Saurat |
| 6,123,707 A | 9/2000 | Wagner |
| 6,132,435 A | 10/2000 | Young |
| 6,139,549 A | 10/2000 | Keller |
| 6,183,472 B1 | 2/2001 | Lutz |
| 6,197,033 B1 | 3/2001 | Haid, Jr. |
| 6,203,543 B1 | 3/2001 | Glossop |
| 6,210,330 B1 | 4/2001 | Tepper |
| 6,251,112 B1 | 6/2001 | Jackson |
| 6,258,090 B1 | 7/2001 | Jackson |
| 6,371,973 B1 | 4/2002 | Tepper |
| 6,440,133 B1 | 8/2002 | Beale |
| 6,440,142 B1 | 8/2002 | Ralph |
| 6,488,682 B2 | 12/2002 | Kikuchi |
| 6,511,484 B2 | 1/2003 | Torode |
| 6,530,929 B1 | 3/2003 | Justis |
| 6,589,249 B2 | 7/2003 | Sater |
| 6,648,888 B1 | 11/2003 | Shluzas |
| 6,660,006 B2 | 12/2003 | Markworth |
| 6,663,656 B2 | 12/2003 | Schmieding |
| 6,726,692 B2 | 4/2004 | Bette |
| 6,743,231 B1 | 6/2004 | Gray |
| 6,746,449 B2 | 6/2004 | Jones |
| 6,752,832 B2 | 6/2004 | Neumann |
| 6,755,829 B1 | 6/2004 | Bono |
| 6,790,208 B2 | 9/2004 | Oribe |
| 6,790,209 B2 | 9/2004 | Beale |
| 6,827,722 B1 | 12/2004 | Schoenefeld |
| 6,910,141 B2 | 6/2005 | Maher |
| 6,932,822 B2 | 8/2005 | Oribe |
| 7,008,422 B2 | 3/2006 | Foley |
| 7,083,621 B2 | 8/2006 | Shaolian |
| 7,156,849 B2 | 1/2007 | Dunbar |
| 7,160,300 B2 | 1/2007 | Jackson |
| 7,179,254 B2 | 2/2007 | Pendekanti |
| 7,179,261 B2 | 2/2007 | Sicvol |
| 7,188,626 B2 | 3/2007 | Foley |
| 7,278,995 B2 | 10/2007 | Nichols |
| 7,296,804 B2 | 11/2007 | Lechot |
| 7,320,689 B2 | 1/2008 | Keller |
| 7,335,208 B2 | 2/2008 | Cavagna |
| 7,371,239 B2 | 5/2008 | Dec |
| 7,430,945 B2 | 10/2008 | Gauthier |
| 7,455,685 B2 | 11/2008 | Justis |
| 7,462,182 B2 | 12/2008 | Lim |
| 7,470,279 B2 | 12/2008 | Jackson |
| 7,473,267 B2 | 1/2009 | Nguyen |
| 7,491,207 B2 | 2/2009 | Keyer |
| 7,491,218 B2 | 2/2009 | Landry |
| 7,497,869 B2 | 3/2009 | Justis |
| 7,527,638 B2 | 5/2009 | Anderson |
| 7,547,318 B2 | 6/2009 | Birkmeyer |
| 7,563,264 B2 | 7/2009 | Landry |
| 7,569,061 B2 | 8/2009 | Colleran |
| 7,572,281 B2 | 8/2009 | Runco |
| 7,591,836 B2 | 9/2009 | Dick |
| 7,604,640 B2 | 10/2009 | Kana |
| 7,608,081 B2 | 10/2009 | Abdelgany |
| 7,621,918 B2 | 11/2009 | Jackson |
| 7,650,821 B2 | 1/2010 | Gauthier |
| 7,651,502 B2 | 1/2010 | Jackson |
| 7,666,188 B2 | 2/2010 | Anderson |
| 7,708,763 B2 | 5/2010 | Selover |
| 7,758,584 B2 | 7/2010 | Bankoski |
| 7,762,164 B2 | 7/2010 | Nino |
| 7,922,731 B2 | 4/2011 | Schumacher |
| 7,927,334 B2 | 4/2011 | Miller |
| 7,931,677 B2 | 4/2011 | Abdelgany |
| 8,043,344 B2 | 10/2011 | Evans |
| 8,087,329 B2 | 1/2012 | Schumacher |
| 2001/0029376 A1 | 10/2001 | Sater |
| 2002/0095153 A1 | 7/2002 | Jones |
| 2002/0120275 A1 | 8/2002 | Schmieding et al. |
| 2003/0009168 A1 | 1/2003 | Beale |
| 2003/0028195 A1 | 2/2003 | Bette |
| 2003/0083747 A1 | 5/2003 | Winterbottom |
| 2003/0125750 A1 | 7/2003 | Zwirnmann |
| 2003/0149438 A1 | 8/2003 | Nichols |
| 2003/0191370 A1 | 10/2003 | Phillips |
| 2003/0199872 A1 | 10/2003 | Markworth |
| 2003/0225408 A1 | 12/2003 | Nichols |
| 2004/0036254 A1 | 2/2004 | Patton |
| 2004/0049191 A1 | 3/2004 | Markworth |
| 2004/0147936 A1 | 7/2004 | Rosenberg |
| 2004/0147937 A1 | 7/2004 | Dunbar |
| 2004/0172057 A1 | 9/2004 | Guillebon |
| 2004/0176779 A1 | 9/2004 | Casutt |
| 2004/0220567 A1 | 11/2004 | Eisermann |
| 2004/0254576 A1 | 12/2004 | Dunbar |
| 2004/0267275 A1 | 12/2004 | Cournoyer |
| 2005/0015095 A1 | 1/2005 | Keller |
| 2005/0021031 A1 | 1/2005 | Foley |
| 2005/0033299 A1 | 2/2005 | Shluzas |
| 2005/0055031 A1 | 3/2005 | Lim |
| 2005/0059969 A1 | 3/2005 | McKinley |
| 2005/0079909 A1 | 4/2005 | Singhaseni |
| 2005/0090824 A1 | 4/2005 | Shluzas |
| 2005/0131408 A1 | 6/2005 | Sicvol |
| 2005/0131420 A1 | 6/2005 | Techiera |
| 2005/0131422 A1 | 6/2005 | Anderson |
| 2005/0137593 A1 | 6/2005 | Gray et al. |
| 2005/0143749 A1 | 6/2005 | Zalenski |
| 2005/0149048 A1 | 7/2005 | Leport |
| 2005/0149053 A1 | 7/2005 | Varieur |
| 2005/0179036 A1 | 8/2005 | Yamazaki |
| 2005/0192570 A1 | 9/2005 | Jackson |
| 2005/0192579 A1 | 9/2005 | Jackson |
| 2005/0228392 A1 | 10/2005 | Keyer |
| 2005/0261702 A1 | 11/2005 | Oribe |
| 2006/0009775 A1 | 1/2006 | Dec |
| 2006/0025768 A1 | 2/2006 | Iott |
| 2006/0036254 A1 | 2/2006 | Lim |
| 2006/0036260 A1 | 2/2006 | Runco |
| 2006/0074418 A1 | 4/2006 | Jackson |
| 2006/0079909 A1 | 4/2006 | Runco |
| 2006/0089651 A1 | 4/2006 | Trudeau |
| 2006/0095035 A1 | 5/2006 | Jones |

(56) References Cited

U.S. PATENT DOCUMENTS

| | | |
|---|---|---|
| 2006/0106380 A1 | 5/2006 | Colleran et al. |
| 2006/0111712 A1 | 5/2006 | Jackson |
| 2006/0111713 A1 | 5/2006 | Jackson |
| 2006/0111714 A1 | 5/2006 | Foley |
| 2006/0111730 A1 | 5/2006 | Hay |
| 2006/0166534 A1 | 7/2006 | Brumfield |
| 2006/0166535 A1 | 7/2006 | Brumfield |
| 2006/0200132 A1 | 9/2006 | Chao |
| 2006/0247630 A1 | 11/2006 | Iott |
| 2006/0278051 A1* | 12/2006 | Gauthier et al. ............... 81/473 |
| 2006/0293692 A1 | 12/2006 | Whipple |
| 2007/0016209 A1 | 1/2007 | Ammann |
| 2007/0043378 A1 | 2/2007 | Kumar |
| 2007/0093849 A1 | 4/2007 | Jones |
| 2007/0129731 A1 | 6/2007 | Sicvol |
| 2007/0161998 A1 | 7/2007 | Whipple |
| 2007/0167954 A1 | 7/2007 | Sicvol |
| 2007/0173831 A1 | 7/2007 | Abdou |
| 2007/0213714 A1 | 9/2007 | Justis |
| 2007/0213722 A1 | 9/2007 | Jones |
| 2007/0233097 A1 | 10/2007 | Anderson |
| 2007/0260261 A1 | 11/2007 | Runco |
| 2007/0270842 A1 | 11/2007 | Bankoski |
| 2007/0270880 A1 | 11/2007 | Lindemann |
| 2008/0004624 A1 | 1/2008 | Olroyd |
| 2008/0009864 A1 | 1/2008 | Forton |
| 2008/0045970 A1 | 2/2008 | Saidha |
| 2008/0077134 A1 | 3/2008 | Dziedzic |
| 2008/0077135 A1 | 3/2008 | Stad |
| 2008/0082103 A1 | 4/2008 | Hutton |
| 2008/0154277 A1 | 6/2008 | Machalk |
| 2008/0154280 A1 | 6/2008 | Schumacher et al. |
| 2008/0200918 A1 | 8/2008 | Spitler |
| 2008/0215061 A1 | 9/2008 | Schumacher et al. |
| 2008/0221583 A1 | 9/2008 | Sharifi-Mehr |
| 2008/0234678 A1 | 9/2008 | Gutierrez |
| 2008/0243190 A1* | 10/2008 | Dziedzic et al. ............. 606/278 |
| 2008/0255574 A1 | 10/2008 | Dye |
| 2008/0288005 A1 | 11/2008 | Jackson |
| 2009/0030419 A1 | 1/2009 | Runco |
| 2009/0030420 A1 | 1/2009 | Runco |
| 2009/0054902 A1 | 2/2009 | Mickiewicz |
| 2009/0082811 A1 | 3/2009 | Stad |
| 2009/0088764 A1 | 4/2009 | Stad |
| 2009/0105712 A1 | 4/2009 | Dauster |
| 2009/0138056 A1 | 5/2009 | Anderson |
| 2009/0143828 A1 | 6/2009 | Stad |
| 2009/0157125 A1 | 6/2009 | Hoffman |
| 2009/0209967 A1 | 8/2009 | Evans et al. |
| 2009/0228055 A1 | 9/2009 | Jackson |
| 2009/0293687 A1* | 12/2009 | Nino et al. ...................... 81/476 |
| 2010/0137915 A1 | 6/2010 | Anderson |
| 2010/0292742 A1 | 11/2010 | Stad |
| 2010/0324609 A1 | 12/2010 | Jones |
| 2011/0172723 A1 | 7/2011 | Miller |

FOREIGN PATENT DOCUMENTS

| | | |
|---|---|---|
| EP | 948939 | 10/1999 |
| EP | 1138267 | 10/2001 |
| EP | 1374786 | 1/2004 |
| EP | 1574175 | 9/2005 |
| EP | 1648320 | 4/2006 |
| EP | 1796564 | 6/2007 |
| FR | 2677242 | 12/1992 |
| FR | 2729291 | 7/1996 |
| WO | WO 9621396 | 7/1996 |
| WO | WO 9737604 | 10/1997 |
| WO | WO 2005006948 | 1/2005 |
| WO | WO 2006020443 | 2/2006 |
| WO | WO 2006127425 | 11/2006 |
| WO | WO 2007040888 | 4/2007 |
| WO | WO 2007121061 | 10/2007 |
| WO | WO 2007040888 | 11/2007 |
| WO | WO 2007149426 | 12/2007 |

* cited by examiner

TORQUE LIMITED INSTRUMENT FOR MANIPULATING A SPINAL ROD RELATIVE TO A BONE ANCHOR

REFERENCE TO RELATED APPLICATIONS

This application is a continuation of U.S. patent application Ser. No. 12/465,098, filed May 13, 2009, which is incorporated herein by reference.

BACKGROUND

Spinal fixation devices are used in orthopedic surgery to align and/or fix a desired relationship between adjacent vertebral bodies. Such devices typically include a spinal connector, such as a spinal rod, that is coupled to adjacent vertebrae by attaching the element to various anchoring devices, such as hooks, bolts, wires, or screws. The spinal rods can have a predetermined contour that has been designed according to the properties of the target implantation site, and once installed, the spinal rod and the anchors holds the vertebrae in a desired spatial relationship, either until desired healing or spinal fusion has taken place, or for some longer period of time.

Spinal connectors, such as spinal rods, can be anchored to specific portions of the vertebra. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a rod-receiving element, usually in the form of a U-shaped slot formed in the head. A set-screw, plug, or similar type of fastening mechanism, is used to lock the spinal rod into the rod-receiving head of the pedicle screw. In use, the shank portion of each screw is threaded into a vertebra, and once properly positioned, a spinal rod is seated through the rod-receiving member of each screw and the rod is locked in place by tightening a set screw or other fastener mechanism to securely interconnect each screw and the spinal rod.

While current spinal fixation systems have proven effective, one challenge associated with such systems is mounting the spinal rods into the rod-receiving member of various fixation devices. In particular, it can be difficult to align and seat the rod into the rod receiving portion of adjacent anchors due to the positioning of the vertebra into which the anchors are mounted. Thus, the use of a spinal rod reduction device, also sometimes referred to as a spinal rod approximator, is often required in order to grasp the head of the anchor and reduce the rod into the rod-receiving head of the bone anchor.

While several rod reduction devices are known in the art, some tend to be bulky and cumbersome to use and, thus, are unsuitable for use all procedures, particularly in minimally invasive surgical procedures in which the skin incisions and tissue pathways to the spine are relatively small and restricted. Accordingly, there is a need for improved rod reduction devices and methods for seating a spinal rod in a rod-receiving member of one or more spinal anchors.

SUMMARY

Disclosed herein are instruments for adjusting the position of a spinal rod relative to a bone anchor that are particularly suited for use in minimally invasive spinal procedures in which the spinal rod is delivered to the bone anchors through screw extensions connected to one or more of the bone anchors. In such procedures, the bone anchors and the screw extensions may be delivered through separate minimally invasive incisions, such as stab incisions. The screw extensions operate as independent pathways to the bone anchor through which instruments and implants, such as the spinal rod and the set screw for each bone anchor, may be delivered to the bone anchor implanted in the vertebra of the patient's spine. The rod adjustment instruments disclosed herein are designed to work within the screw extensions without the need to expand or enlarge the skin incisions or tissue pathways from the skin incisions to the bone anchors implanted in the vertebra of the patient's spine.

Accordingly, an instrument for adjusting the position of a spinal rod relative to a bone anchor may include a generally tubular screw extension connectable to the bone anchor, a reduction cap removably connectable to the screw extension, a set screw driver, an externally threaded collar positioned about and rotatable relative to the drive shaft of the set screw driver and engagable with an internal thread provided on the bore of the reduction cap, and a handle connectable to the set screw driver and the collar. The handle may include an inner shaft having a distal end configured to engage the proximal end of the driver shaft of the set screw driver, an outer shaft having a distal end configured to engage the threaded collar, and a clutch connecting the inner shaft to the outer shaft and permitting selective rotation of the inner shaft relative to the outer shaft, and thus, selective rotation of the set screw driver relative to the collar, upon application of a torque to the outer shaft greater than a preselected torque value.

BRIEF DESCRIPTION OF THE FIGURES

These and other features and advantages of the instruments and methods disclosed herein will be more fully understood by reference to the following detailed description in conjunction with the attached drawings in which like reference numerals refer to like elements through the different views. The drawings illustrate principles of the instruments and methods disclosed herein and, although not to scale, show relative dimensions.

DETAIL DESCRIPTION OF EXEMPLARY EMBODIMENTS

Certain exemplary embodiments will now be described to provide an overall understanding of the principles of the structure, function, manufacture, and use of the instruments and methods disclosed herein. One or more examples of these embodiments are illustrated in the accompanying drawings. Those of ordinary skill in the art will understand that the instruments and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The articles "a" and "an" are used herein to refer to one or to more than one (i.e. to at least one) of the grammatical object of the article. By way of example, "an element" means one element or more than one element.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

FIGS. 1-5 illustrate an exemplary embodiment of a spinal fixation system including a plurality of bone anchors 12, each of which is implanted in a vertebra VB of a patient's spine, a spinal rod 10 connecting the bone anchors, and a plurality of screw extensions 14, each connected to one of the bone anchors. The exemplary spinal fixation system is a minimally invasive spinal system that allows a spinal surgeon to align and/or fix a number of vertebrae of a patient's spine to treat a wide range of spinal pathologies, including the treatment of degenerative disc disease and the correction of spinal deformities. In the exemplary system, the implanted bone anchors 12 are polyaxial pedicle screws, such as the VIPER polyaxial pedicle screws available from DePuy Spine, Inc., of Raynham, Mass. The exemplary polyaxial pedicle screws 12 include a U-shaped channel for receiving the spinal rod 10 therein and a set screw 18. The U-shaped channel is defined by two spaced apart arms and the set screw 18 is engageable with an internal thread provided on the arms to secure the spinal rod 10 within the U-shaped channel and to the polyaxial bone screw 12. Suitable polyaxial pedicle screws are described in U.S. Pat. No. 7,179,261, which is incorporated herein by reference. Other types of bone anchors also may be used including monoaxial screws, uniplanar screws, and hooks. In addition to the set screw 18, other types of closure mechanisms, including a twist-in cap, the Monarch Typhoon Cap closure available from DePuy Spine, Inc, of Raynham, Mass. or a two piece set screw, such as the Expedium Dual Innie closure available from DePuy Spine, Inc, of Raynham, Mass.

Figure 1:
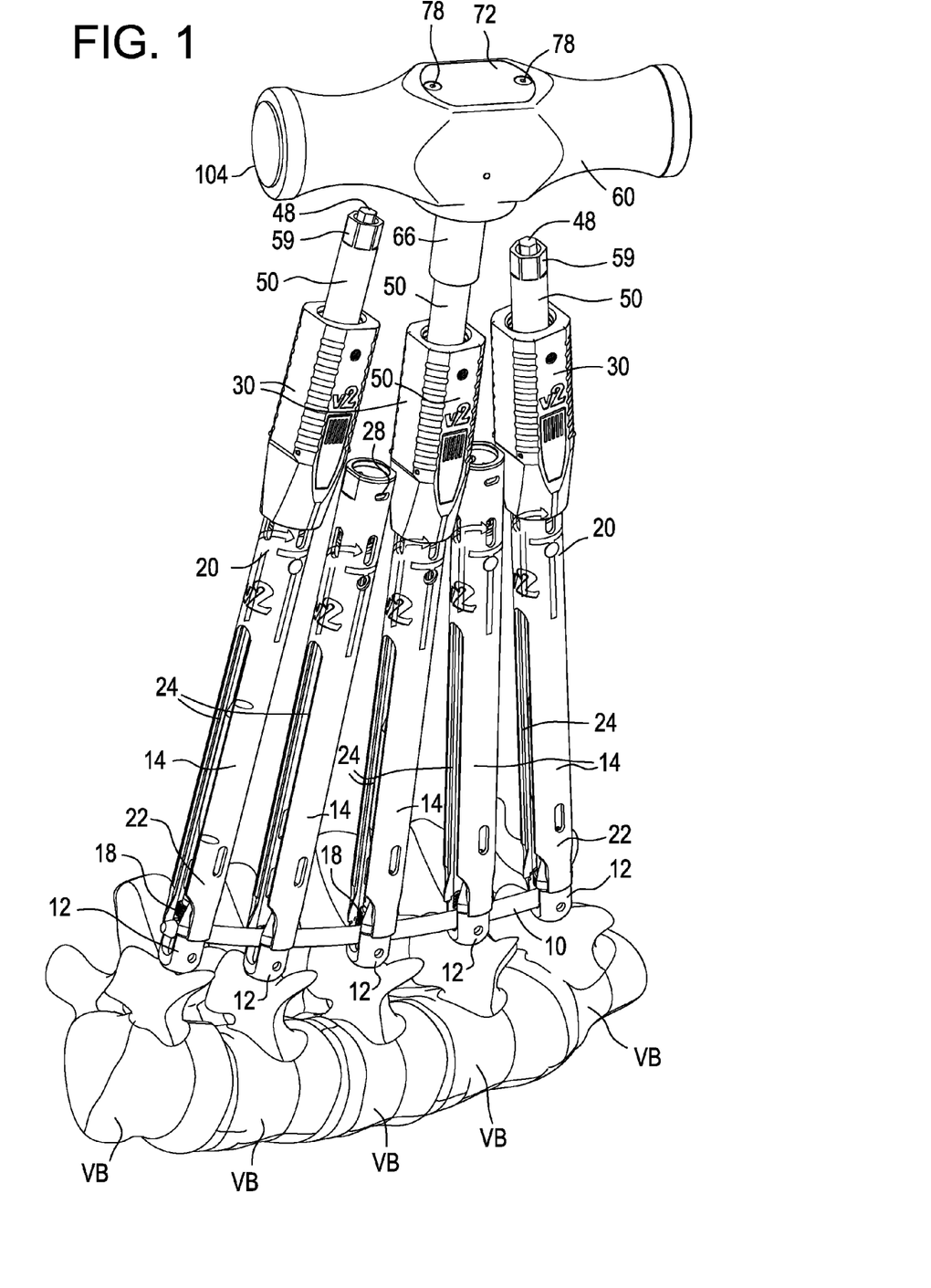
FIG. 1 is a perspective view of an exemplary spinal fixation system including a plurality of bone anchors, each connected to a vertebra, a plurality of screw extensions, each connected one of the bone anchors, a spinal rod connecting the bone anchor together, and plurality of instruments for adjusting the spinal rod relative to the bone anchors.
Figure 2:
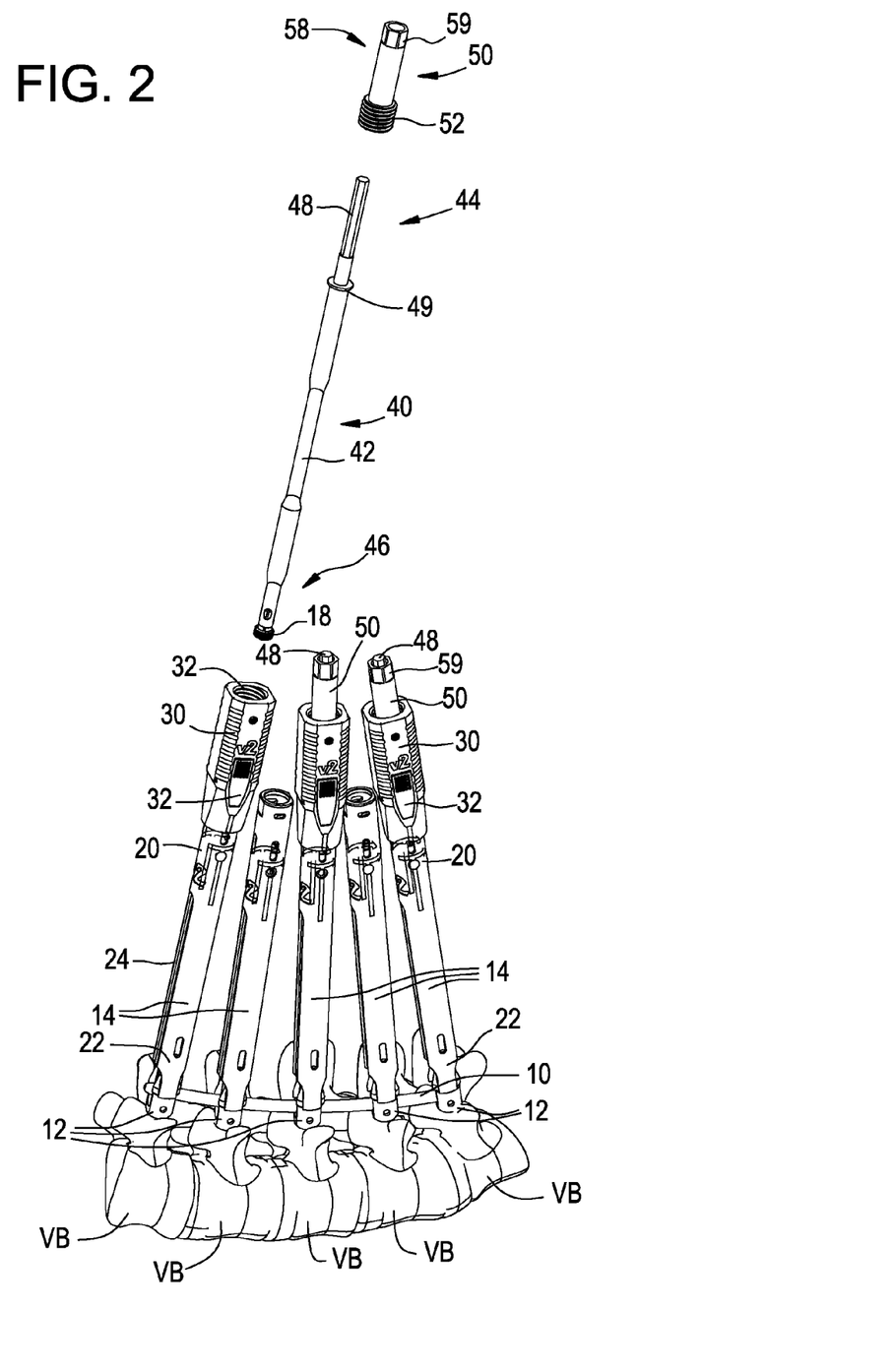
FIG. 2 is a perspective view of the spinal fixation system of FIG. 1, illustrating the positioning of a set screw driver and a threaded collar within a reduction cap and the screw extension to which the reduction cap is connected.

The exemplary screw extensions 14 are generally tubular in shape and have a central lumen extending from the proximal end 20 of the screw extension 14 to the distal end 22 of the screw extension 14. The central lumen of each screw extension 14 is sized to receive instruments and implants therethrough. The screw extensions 14 may include a pair of opposed longitudinal slots 24 that open to the central lumen of the screw extension 14. The slots 24 open at the distal end 22 of the screw extension 14 and extend axially from the distal end 22 of the screw extension. The screw extensions provide a number of functions including facilitating the delivery of the spinal rod 10 to the bone anchors 12 in a minimally invasive manner. In one exemplary minimally invasive surgical technique, each bone anchors 12 and each screw extension 14 may be delivered percutaneously to a vertebra of the spine through a separate and independent minimally invasive incision, such as a stab incision. The spinal rod 10 may be introduced to the bone anchors 12 through one of the screw extensions 14, or through one of the minimally invasive incisions, and guided into position beneath the skin and fascia. Exemplary screw extensions are described in U.S. Pat. No. 7,179,261 and U.S. Patent Application Publication No. 2008/0077134 and U.S. patent application Ser. No. 12/244,268, each of which is incorporated herein by reference. Exemplary minimally invasive surgical techniques are described in U.S. Pat. No. 7,527,638, U.S. Patent Application Publication No. 2005/0131422, and U.S. Patent Application Publication No. 2009/0082811, each of which is incorporated herein by reference.

The exemplary spinal system includes an instrument for adjusting the position of the spinal rod 10 relative to one or more of the bone anchors 12. The instrument may include a reduction cap 30 removably connectable to the proximal end 20 of one of the screw extensions 14, a set screw driver 40, an externally threaded collar 50 positioned about and rotatable relative to the drive shaft 42 of the set screw driver 40 and a handle 60 connectable to the set screw driver 40 and the collar 50.

The reduction cap 30 has an internal bore extending therethrough that includes an internal thread 32 for engaging an external thread 52 provided on the collar 50. The reduction cap 30 may include a mating element 32 disposed on the distal end of the reduction cap 30 and adapted to removably mate the reduction cap to one or more of the screw extensions 14. The mating element 32 may include a pawl disposed within the bore of the cap 30 that can engage a groove or slot 28 provided on the proximal end 20 of the screw extension 14. Alternatively, the mating element 32 may be one or more threads for engaging a corresponding thread on the proximal end 20 of the screw extension 14, a ball and plunger configuration, or other suitable mechanisms for removably connecting the reduction cap 30 to the screw extension in a manner that permits axial adjustment of the spinal rod with the set screw driver 40. Exemplary reduction caps are disclosed in U.S. Patent Application Publication No. 2008/0243190, which is incorporated herein by reference.

In alternative embodiments, the central lumen of screw extension 14 may include an internal thread to facilitate reduction of the spinal rod 10 relative to the bone anchor 12. In such embodiments, the internal thread may be provided at the proximal end 20 of the screw extension 14, for example, and may be engaged by the externally threaded collar 50, thereby eliminating the need for the reduction cap 30.

Figure 4:
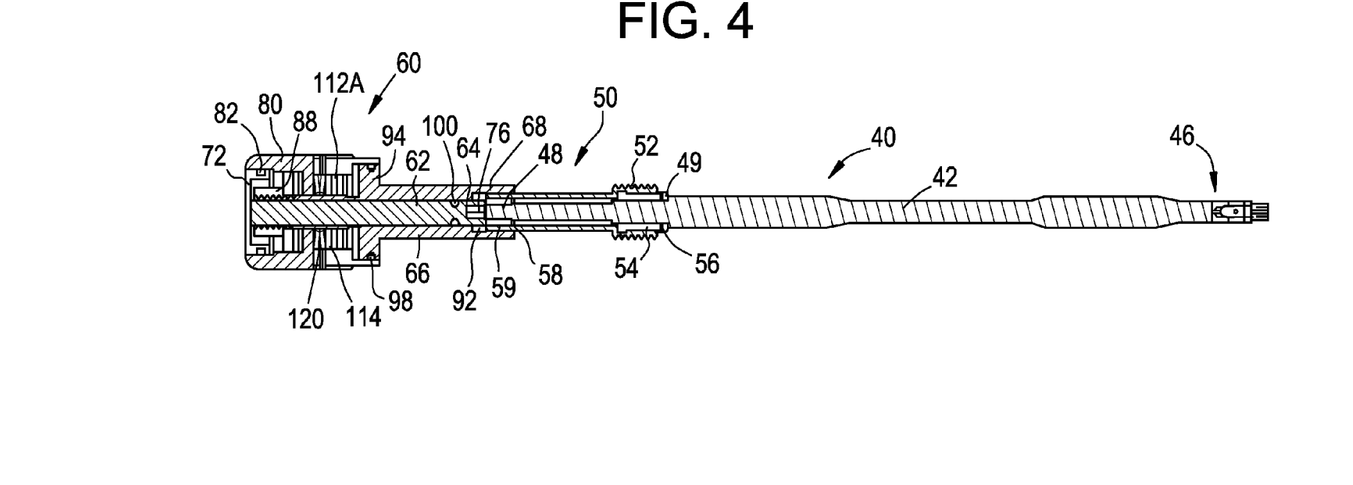
FIG. 4 is a side view in cross section of the instrument of FIG. 3 taken along line A-A in FIG. 3.
Figure 5:
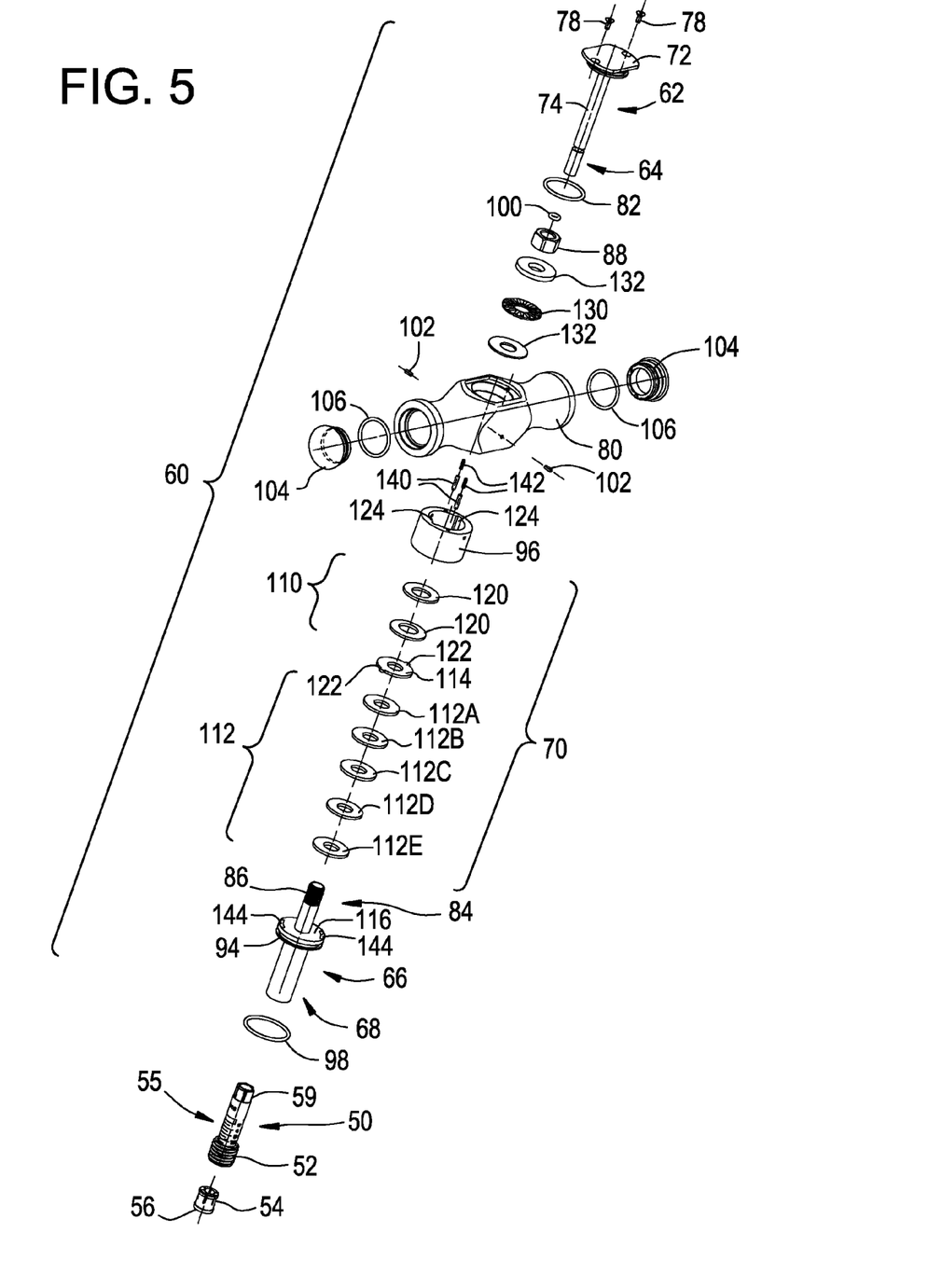
FIG. 5 is an exploded view of the instrument of FIG. 3 with the set screw driver removed.

The exemplary set screw driver 40 includes a drive shaft 42 extending from a proximal end 44 to a distal end 46. The proximal end 44 of the set screw driver 40 includes a drive feature that facilitates rotation of the set screw driver 40 by the handle 60. In the exemplary embodiment, the drive feature is hexagonal shaped, in cross section, post 48 that is sized and shaped to fit within a complementary shaped recess 76 within the inner shaft 62 of the handle 60. The distal end 46 of the set screw driver is sized and shaped to fit within the mating feature of the set screw 18. In the exemplary embodiment, the distal end 46 is configured to retain the set screw 18 until released by axially advancing the distal end 46 relative to the set screw 18. An axial stop 49, in the form of a shoulder or a rib, is provided on the drive shaft 42 of the set screw driver 40.

The threaded collar 50 is generally tubular in shape and includes a central lumen. The threaded collar 50 may be positioned about the drive shaft 42 of the set screw driver 40 and may rotate relative to the drive shaft 42 of the set screw driver 40. To facilitate rotation of the collar 50 relative to the drive shaft 42, the collar 50 may include a bushing 54 positioned within the central lumen of the threaded collar 50. The distal end 56 of bushing 54 engages the axial stop 49 of the set screw driver 40. The proximal end 58 of the threaded collar 50 includes a drive feature that facilitates rotation of the collar 50 by the handle 60. In the exemplary embodiment, the drive feature is a hexagonal shaped, in cross section, section 59 that is sized and shaped to fit within a complementary shaped recess 92 within the outer shaft 66 of the handle 60. The outer surface of the threaded collar 50 may include indicia 55 to indicate the position of the threaded collar 50, as well as the set screw 18, relative to the screw extension 14 and the screw 12. The indicia 55 may be a series of depth markers indicating the depth of collar 50 relative to the screw extension 14.

The handle 60 may include an inner shaft 62 having a distal end 64 configured to engage the proximal end 44 of the driver shaft 42 of the set screw driver 40, an outer shaft 66 having a distal end 68 configured to engage the threaded collar 50, and a clutch 70 connecting the inner shaft 62 to the outer shaft 66 and permitting selective rotation of the inner shaft 62 relative to the outer shaft 66, and thus, selective rotation of the set screw driver 40 relative to the collar 50.

The inner shaft 62, in the exemplary embodiment, includes a proximal flange 72 and a cylindrical body 74 that terminates with a recess 76 configured to engage the post 48 of the set screw driver 40 and transmit rotational motion thereto. The proximal flange 72 may be secured to the top of handle body 80 by fasteners 78 and an O-ring 82 may be positioned between the flange 72 and the handle body 80.

The outer shaft 66, in the exemplary embodiment, may be generally tubular in shape having a central lumen sized and shaped to receive the inner shaft 62 therein. The proximal end 84 of the outer shaft 66 includes an external thread 86 for engagement with a torque adjustment mechanism, a nut 88 in the exemplary embodiment, as described in more detail below. The distal end 68 of the outer shaft 66 includes a recess 92 configured to engage the hexagonal section 59 of the collar 50 and transmit rotational motion thereto. The outer shaft 66 may include a flange 94 that engages a clutch housing 96 secured to the bottom of the handle body 80. An O-ring 98 may be positioned between the flange 94 and the clutch housing 96 and an O-ring 100 may be positioned between the inner shaft 62 and the outer shaft 66.

The handle clutch 70 is positioned within the cylindrically shaped clutch housing 96, which is secured within the handle body 80. Dowel pins 102 extend through the handle body 80 into the clutch housing 96 to prevent rotation of the clutch housing relative to the handle body 80. Two handle caps 104 and complementary O-rings 106 connect to the handle body 80 to seal the handle body 80.

O-rings 82, 98, 100, and 106 seal the handle body 80 to prevent fluids from entering the handle body 80 during sterilization procedures.

The handle clutch 70 may include a spring 110 and a plurality of disc clutch members 112 positioned about the outer shaft 66. The spring 110 biases the disc clutch members 112 into contact with one another and into contact with the outer shaft 66, in particular into contact with the flange 94. During use of the instrument, at least one disc clutch member 112A may rotate relative to an adjacent disc clutch member 112B upon application of a torque to the collar 50 and outer shaft 66 greater than a preselected torque value, thereby allowing the inner shaft 62 and the set screw driver 40 to rotate relative to the outer shaft 66 and the collar 50.

In the exemplary embodiment, the clutch 70 includes five adjacent disc clutch members 112A-112E. In alternative embodiments, any number of adjacent disc clutch members may be employed. For example, in one alternative embodiment, two disc clutch members may be employed. Moreover, in certain alternative embodiments, the proximal facing surface 116 of the axial stop 94 of the outer shaft 66 may have a disc clutch member connected thereto or may otherwise function as a disc clutch member by, for example, coating the proximal facing surface 116 with an appropriate wear resistant material, such as a ceramic or polymer coating. In such embodiments, the proximal facing surface 116 may engage a single disc clutch member 112E interposed between the anti-rotation washer 114 and the proximal facing surface 116, without any further disc clutch members being provided. Likewise, the distal facing surface of the anti-rotation washer 114, if included, may have a disc clutch member connected thereto or may otherwise function as a disc clutch member by, for example, coating the distal facing surface with an appropriate wear resistant material, such as a ceramic or polymer coating. In such embodiments, the distal facing surface of the anti-rotation washer 114 may engage a single disc clutch member 112 interposed between the anti-rotation washer 114 and the proximal facing surface 116, without any further disc clutch members being provided or may directly engage the proximal facing surface 116 with the proximal facing surface 116 operating as a disc clutch member.

The disc clutch members 112A-E may be constructed from a material selected to reduce wear on the clutch members. For example, the disc clutch members 112A-E may be constructed from metal, such as steel, from a ceramic material, from a polymer material, or from a composite material such as fiberglass. In certain embodiments, the disc clutch members may be constructed from the same material. In other embodiments, one or more of the clutch members may be selected from different materials. For example, disc clutch members 112A, 112C, and 112E may be constructed from a first material, such as fiberglass, and disc clutch members 112B and 112D may be constructed from a second material, distinct from the first material, such as steel.

In the exemplary embodiment, the spring 110 includes as pair of Belleville springs 120 positioned about the outer shaft 66. Any number of Belleville springs, including a single Belleville spring, may be employed to provide a compressive force on the disc clutch members 112A-E. In the exemplary embodiment, the Belleville springs 120 bias the disc clutch members 112A-E into contact with the proximal facing surface 116 of the axial stop 94 of the outer tube 66 to thereby provide an axially compressive force on the disc clutch members. One or more springs other than Belleville springs may be employed to provide the compressive force on the clutch members.

The clutch 70 may include an anti-rotation washer 114 positioned between spring 110 and the disc clutch members to prevent wearing of the spring 110 by engagement with a rotating clutch member. In the exemplary embodiment, the anti-rotation washer 114 is positioned between the distal Belleville washer 120 and the proximal disc clutch member 112A. The anti-rotation washer 114 may include one or more projections 122 that are sized and shaped to fit within complementary axial slots 124 provided in the clutch housing 96.

The exemplary instrument may include an adjustment member for adjusting the reselected torque value above which one or more of the clutch members may rotate. In the exemplary embodiment, the adjustment member is nut 88 that engages the external thread 86 on the proximal end 84 of the outer shaft 66. Advancing the nut 88 toward the clutch members 112 and the spring 110 increases the axial compressive force on the clutch members 112, thereby increasing the torque above which one or more of the clutch members may rotate. Conversely, moving the nut 88 away from the clutch members 112 and the spring 110 decreases the axial compressive force on the clutch members 112, thereby decreasing the torque above which one or more of the clutch members may rotate. A thrust bearing 130 and a pair of bearing races 132, provided on either side of the thrust bearing 130, may be positioned between the nut 88 and the spring 110. The thrust bearing 130 and bearing races 132 inhibit rotation of the nut 88 during operation of the clutch 70.

Figure 6:
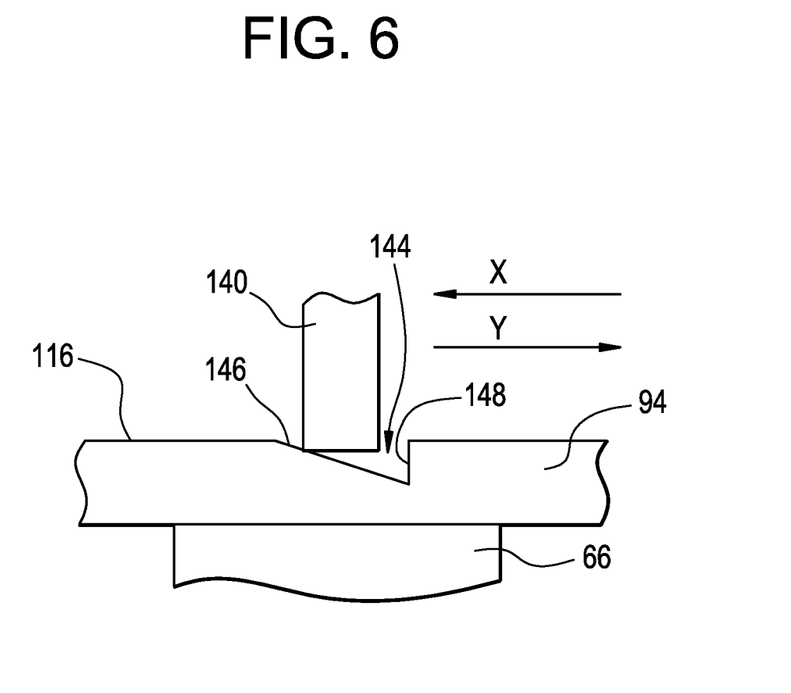
FIG. 6 is a side view of the outer shaft of the clutch of the instrument of FIG. 3.

The exemplary instrument may include a mechanism to inhibit rotation of the outer shaft 66 in one direction. In the exemplary embodiment, the mechanism includes a pair of pins 140 positioned within the wall of the clutch housing 96 that extend from the distal end of the clutch housing 96 to engage the proximal facing surface 116 of the flange 94 of the outer shaft 66. Springs 142 bias the pins 140 into contact with the proximal facing surface 116 of the flange 94 of the outer shaft 66. The proximal facing surface 116 of the flange 94 includes a pair of opposed ramped indents 144, each having an angled surface 146, oriented at an angle to the proximal facing surface 116, and a stop surface 148, oriented approximately perpendicular to the proximal facing surface, as best illustrated in FIG. 6. During rotation of outer shaft 66 in a first direction, indicated by Arrow X, the pin 140 may move through the indent 144 via the angled surface 146. Rotation of the outer shaft 66 in the opposite direction, indicated by the Arrow Y, causes the pin 140 to contact the stop surface 148, which prevents further motion of the pin 140, and the outer shaft 66, relative to the handle housing 80. In this manner, the clutch 70 may function in one rotational direction (Arrow X) but not the other rotational direction (Arrow Y).

One exemplary method of using the exemplary instrument may include connecting one of the screw extensions 14 to a bone anchor 12 and implanting the bone anchor 12 into a vertebra VB, as illustrated in FIG. 1. As discussed above, the bone anchors 12, the screw extensions 14, and the spinal rod 10 using minimally invasive surgical technique, including, for example, delivering the screw extensions 14 and the bone anchors 12 through separate minimally invasive incisions. Any number of bone anchors 12 and corresponding screw extensions 14 may be employed depending on the procedure being performed. A spinal rod 10 may be delivered into proximity to the bone anchors 12 by, for example, positioning the spinal rod 10 through the longitudinal slots 24 of the screw extensions 14.

A reduction cap 30 may be connected to one or more of the screw extensions 14. As illustrated in FIGS. 1 and 2, a set screw driver 40 may be positioned through the reduction cap 30 and the screw extension 14 with a set screw 18 engaged to a distal end 46 of the set screw driver 40. An externally threaded collar 50 may be positioned about the set screw driver 40. The collar 50 is rotatable relative to the driver 40 and advanced to engaging an axial stop 49 on the driver 40.

Figure 3:
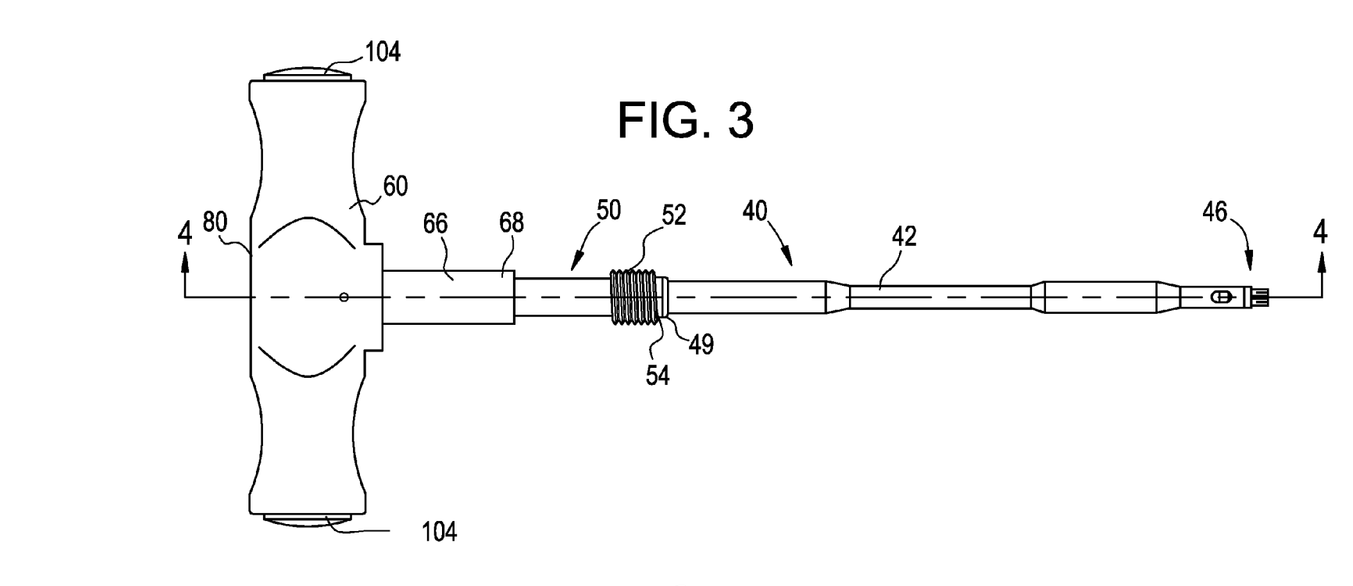
FIG. 3 is a side view of one of the instruments for adjusting the spinal rod relative to the bone anchors, illustrating the handle connected to set screw driver and the threaded collar.

The handle 60, including the clutch 70, may be positioned about the distal ends of the collar 50 and the set screw driver 40. The distal end 64 of the inner shaft 74 engages the post 48 at the proximal end 44 of the set screw driver 40 and the distal end 68 of the outer shaft 66 engages the post 59 at the proximal end of the collar 50. The handle 60 connected to the set screw driver 40 and the collar 50 may be rotated in a first direction, e.g., a clockwise direction, to engage the external thread 52 of the collar 50 with the internal thread 32 of the reduction cap 30. The handle 60 may continue to be rotated in the first direction to axially advance the set screw driver 40 and the collar 50 distally within the screw extension 14 and to advance the set screw 18 into contact with the spinal rod 10. The axial advancement of the set screw 18 against the spinal rod 10 axially positions the spinal rod 10 within the bone anchor 12.

By continuing to rotate the handle 60 in the first direction, the set screw 18 may be advanced into engagement with an internal thread of the bone anchor 12. Engagement of the set screw 18 with the internal thread on the bone anchor 12 may increase the torque on the collar 50, which is threadedly engaged to the reduction cap 30, thereby increasing the torque on the outer shaft 66 of the clutch 70. If the increase torque exceeds the preselected torque value, at least one disc clutch member 112 of the clutch 70 will rotate relative to an adjacent disc clutch member 112 of the clutch 70, thereby allowing the set screw driver 40 to rotate independently of the collar 50 and thereby advance the set screw 18 into engagement with bone anchor 12 and capture the spinal rod 10 within the bone anchor 12. As the torque on the collar 50 and the outer shaft 66 decreases below the preselected torque value, the clutch members 112 will rotate together, allowing the collar 50 and set screw driver 40 to rotate together. During advancement of the set screw 18 into its final position capturing the spinal rod 12, the torque on the collar 50 and outer shaft 66 may cycle above and below the preselected torque value and, correspondingly, the clutch 70 will permit rotation of the collar 50 relative to the set screw driver 40 to reduce the torque and prohibit such rotation when the torque is below the preselected torque value.

Once the set screw 18 is properly positioned, the set screw driver 40 and collar 50 may be removed from the screw extension 14 and the screw extension 14 may be disconnected from the bone anchor 12.

While the exemplary method has been described in connection with minimally invasive surgical procedures in which the screw extensions 14 and the bone anchors 12 are delivered through minimally invasive incisions, such as separate stab incisions, the instruments disclosed herein may be used in non-minimally invasive procedures, e.g., open procedures, in which the screw extensions 14 and the bone anchors 12 are delivered through one or more large incisions. In such open procedures, the screw extensions 14 may be connected to the bone anchors 12 after implantation of the bone anchors 12 and/or delivery of the spinal rod 10 to the bone anchors 12. In such exemplary embodiments, the screw extensions 14 need not include extended longitudinal slots 24. Instead, the slots 24 may extend a minimal distance from the distal end 22 of the screw extension 14 sufficient to permit rod reduction. Exemplary screw extensions for such open procedures are described in U.S. Patent Application Publication No. 2006/0200132 and U.S. Patent Application Publication No. 2007/016209, each of which is incorporated herein by reference.

While the instruments and methods of the present invention have been particularly shown and described with reference to the exemplary embodiments thereof, those of ordinary skill in the art will understand that various changes may be made in the form and details herein without departing from the spirit and scope of the present invention. Those of ordinary skill in the art will recognize or be able to ascertain many equivalents to the exemplary embodiments described specifically herein by using no more than routine experimentation. Such equivalents are intended to be encompassed by the scope of the present invention and the appended claims.

What is claimed is:
1. A spinal fixation system comprising:
a spinal rod,
a plurality of bone anchors, one or more of the bone anchors having a U-shaped channel for receiving the spinal rod therein and a set screw, the U-shaped channel defined by two spaced-apart arms, the set screw having an external thread engagable with an internal thread provided on the arms to secure the spinal rod in the U-shaped channel, a plurality of generally tubular screw extensions, each screw extension connectable to one of the bone anchors and having a central lumen extending from a proximal end to a distal end of the screw extension, the central lumen sized to receive instruments and implants therethrough, a reduction cap having a bore extending therethrough and a mating element disposed on a distal end thereof and adapted to removably mate the cap to one of the screw extensions, the bore including an internal thread, a set screw driver comprising a drive shaft having a proximal end and terminating at a distal end sized and shaped to fit within a mating feature on the set screw of a bone anchor, an externally threaded collar positioned about the drive shaft and rotatable relative to the drive shaft, the collar engaging an axial stop on the drive shaft, the collar engagable with the internal thread of the reduction cap, and a handle comprising an inner shaft having a distal end configured to engage the proximal end of the driver shaft of the set screw driver, an outer shaft having a distal end configured to engage the threaded collar, and a clutch connecting the inner shaft to the outer shaft and permitting selective rotation of the inner shaft relative to the outer shaft upon application of a torque to the outer shaft greater than a preselected torque value, the clutch comprising a spring and a plurality of disc clutch members positioned about the outer shaft, the spring biasing the disc clutch members into contact with one another and into contact with the outer shaft, at least one disc clutch member rotating relative to an adjacent disc clutch member upon application of a torque to the outer shaft greater than a preselected torque value.

2. The system of claim 1, wherein the outer shaft of the handle includes an axial stop, at least one of the disc clutch members being biased into engagement with the axial stop by the spring.

3. The system of claim 2, wherein one of the disc clutch members is coupled to the axial stop.

4. The system of claim 1, wherein the handle includes an adjustment member for adjusting the preselected torque value.

5. The system of claim 4, wherein the adjustment member is a nut engaged with an external thread on the outer shaft of the handle, the nut applying an axial force on the clutch, wherein adjustment of the axial position of the nut on the outer shaft adjusts the axial force on the clutch.

6. The system of claim 1, wherein the spring comprises one or more Belleville springs positioned about the outer shaft.

7. The system of claim 1, wherein each screw extension has a pair of opposed longitudinal slots opening to the lumen of the screw extension, the slots opening at the distal end of the screw extension and extending axially from the distal end of the screw extension.

8. An instrument for adjusting the position of a spinal rod relative to a bone anchor, the instrument comprising:

a generally tubular screw extension connectable to the bone anchor and having a central lumen extending from a proximal end to a distal end of the screw extension, a reduction cap having a bore extending therethrough and a drive element, the reduction cap removably connectable to the screw extension, a set screw driver comprising a drive shaft having a proximal end and terminating at a distal end sized and shaped to fit within a mating feature on a set screw for the bone anchor, a collar positioned about the drive shaft and rotatable relative to the drive shaft, the collar engaging an axial stop on the drive shaft, the collar engagable with the drive feature of the reduction cap, and a handle comprising an inner shaft having a distal end configured to engage the proximal end of the driver shaft of the set screw driver, an outer shaft having a distal end configured to engage the collar, and a clutch connecting the inner shaft to the outer shaft and permitting selective rotation of the inner shaft relative to the outer shaft upon application of a torque to the outer shaft greater than a preselected torque value, the clutch comprising a spring and a plurality of disc clutch members positioned about the outer shaft, the spring biasing the disc clutch members into contact with one another and into contact with the outer shaft, at least one disc clutch member rotating relative to an adjacent disc clutch member upon application of a torque to the outer shaft greater than a preselected torque value.

9. The instrument of claim 8, wherein the outer shaft of the handle includes an axial stop, the disc clutch members being biased into engagement with the axial stop by the spring.

10. The instrument of claim 9, wherein one of the disc clutch members is coupled to the axial stop.

11. The instrument of claim 8, wherein the handle includes an adjustment member for adjusting the preselected torque value.

12. The instrument of claim 11, wherein the adjustment member is a nut engaged with an external thread on the outer shaft of the handle, the nut applying an axial force on the clutch, wherein adjustment of the axial position of the nut on the outer shaft adjusts the axial force on the clutch.

13. The instrument of claim 8, wherein the spring comprises one or more Belleville springs positioned about the outer shaft.

14. The instrument of claim 8, wherein the screw extension has a pair of opposed longitudinal slots opening to the lumen of the screw extension, the slots opening at the distal end of the screw extension and extending axially from the distal end of the screw extension.

15. An instrument for adjusting the position of a spinal rod relative to a bone anchor, the instrument comprising:

a generally tubular screw extension connectable to the bone anchor and having a central lumen extending from a proximal end to a distal end of the screw extension, the central lumen including an internal thread at the proximal end thereof, a set screw driver having a proximal end and terminating at a distal end sized and shaped to fit within a mating feature on a set screw for the bone anchor, an externally threaded collar positioned about the set screw driver and rotatable relative to the set screw driver, the collar engaging an axial stop on the set screw driver, the collar engagable with the internal thread of the screw extension, and a handle comprising an inner shaft having a distal end configured to engage the proximal end of the set screw driver, an outer shaft having a distal end configured to engage the threaded collar, and a clutch connecting the inner shaft to the outer shaft and permitting selective rotation of the inner shaft relative to the outer shaft upon application of a torque to the outer shaft greater than a preselected torque value, the clutch comprising a spring and a plurality of disc clutch members positioned about the outer shaft, the spring biasing the disc clutch members into contact with one another and into contact with the outer shaft, at least one disc clutch member rotating relative to an adjacent disc clutch member upon application of a torque to the outer shaft greater than a preselected torque value.

16. The instrument of claim 15, wherein the outer shaft of the handle includes an axial stop, the disc clutch members being biased into engagement with the axial stop by the spring.

17. The instrument of claim 16, wherein one of the disc clutch members is coupled to the axial stop.

18. The instrument of claim 15, wherein the handle includes an adjustment member for adjusting the preselected torque value.

19. The instrument of claim 18, wherein the adjustment member is a nut engaged with an external thread on the outer shaft of the handle, the nut applying an axial force on the clutch, wherein adjustment of the axial position of the nut on the outer shaft adjusts the axial force on the clutch.

20. The instrument of claim 15, wherein the spring comprises one or more Belleville springs positioned about the outer shaft.

21. The instrument of claim 15, wherein the screw extension has a pair of opposed longitudinal slots opening to the lumen of the screw extension, the slots opening at the distal end of the screw extension and extending axially from the distal end of the screw extension.

* * * * *